United States Patent [19]

Ambrisco et al.

[11] Patent Number: 5,324,266
[45] Date of Patent: Jun. 28, 1994

[54] IN-LINE SAMPLING SYSTEM INCORPORATING AN IMPROVED BLOOD SAMPLING DEVICE

[75] Inventors: William M. Ambrisco, Hayward; Lauretta Iwamasa, Newark; Anthony J. Pantages, Mountain View, all of Calif.

[73] Assignee: Abbott Laboratories, Abbott Park, Ill.

[21] Appl. No.: 991,610

[22] Filed: Dec. 23, 1992

[51] Int. Cl.⁵ .................. A61M 1/00; A61M 5/178; A61M 5/00; A61M 5/315
[52] U.S. Cl. ................... 604/125; 604/184; 604/211; 604/231; 604/900
[58] Field of Search ............... 604/231, 208, 211, 38, 604/184, 187, 218, 900, 124, 125; 128/765

[56] References Cited

U.S. PATENT DOCUMENTS

| | | | |
|---|---|---|---|
| 2,861,571 | 11/1958 | Sandhage et al. | 604/184 |
| 4,257,426 | 3/1981 | Bailey | 604/184 |
| 4,457,755 | 7/1984 | Wilson | 604/184 |
| 4,744,955 | 5/1988 | Shapiro | 604/208 |
| 4,934,379 | 6/1990 | Marzolf et al. | 604/231 |
| 5,032,117 | 7/1991 | Motta | 604/187 |
| 5,147,329 | 9/1992 | Brannon | 604/231 |

FOREIGN PATENT DOCUMENTS

| | | | |
|---|---|---|---|
| 1046541 | 12/1953 | France | 604/184 |
| 705322 | 5/1966 | Italy | 604/38 |
| 76711 | 12/1954 | Netherlands | 604/184 |

*Primary Examiner*—Gene Mancene
*Assistant Examiner*—Todd E. Manahan
*Attorney, Agent, or Firm*—Robert E. Wexler; Harry G. Thibault

[57] ABSTRACT

A blood sampling system incorporates a fluid storage mechanism which can be disposed along the longitudinal axis of a fluid line extending from an injection site to a fluid supply. Both the main body portion of the fluid storage mechanism and a fluid draw element of the fluid storage mechanism are axially aligned with the longitudinal axis of the fluid line. The fluid storage mechanism also incorporates a vortex inducer element at the distal end of the fluid draw element to induce a swirl of fluid to cleanse the fluid storage mechanism once a sample drawn into the fluid storage mechanism has been returned to the patient. An alternative embodiment of the fluid storage mechanism includes a volume control device.

9 Claims, 8 Drawing Sheets

FIG._11C ns-LINE SAMPLING SYSTEM INCORPORATING AN IMPROVED BLOOD SAMPLING DEVICE

BACKGROUND OF THE INVENTION

1. Field of the Invention

The present invention relates to blood sampling systems and, in particular, to an improved blood sampling device usable in such systems, and enabling in-line sampling.

2. State-of-the-Art

Arterial and venous infusion lines are used to introduce fluids into the blood stream of a patient. Devices of various types have long been used to regulate the flow of fluid from a fluid supply to an injection site. Typically the injection site is also used to take periodic blood samples from the patient.

In such an instance, the flow of fluid from the fluid supply can be turned off to allow blood to flow in the reverse direction through the arterial line to facilitate taking such blood samples. Patient requirements and the treatment protocol prescribed will dictate the frequency of the blood sampling procedure. When the frequency of sampling becomes greater, according to the needs of the patient and the treatment protocol, it becomes desirable to improve the efficiency of the blood draw procedure and eliminate waste whenever possible.

A particular situation of note relates to neonatal patients in which the blood supply is considerably smaller than the blood supply of adults and the need to maximize efficiency in the blood sampling procedure and to avoid unnecessary discharge of blood is of particular concern.

A known sampling procedure for drawing blood from an arterial line utilizes a plurality of stopcock mechanisms that prevent the flow of fluid from the fluid source and allow blood to flow from the patient into a collecting syringe connected to a removal port formed in one of the stopcocks. However, such a procedure necessarily will draw a mixture of fluid and blood in the first iteration of the sampling procedure, and the initial sample is discarded. A second sample is then taken, such second sample considered to be a representative sample of blood. Because the discarded sample includes not only fluid from the fluid source, but some of the patient's blood, such a two-sample process causes an unnecessary loss of blood to the patient. Other undesirable effects associated with the above noted sampling process includes the increased potential for introduction of air into the arterial line and the increased potential for introduction of contaminants into the patient's bloodstream.

An effort to modify the above noted two-step sampling process is noted in U.S. Pat. No. 4,673,386 entitled "Blood Sampler Device" and issued to Gordon. Gordon describes a mechanism for eliminating the need to undertake a two-step process to withdraw blood through an arterial line. The Gordon device comprises a combination pump/storage mechanism which accommodates the return flow of the downstream fluid such that a single sample can be taken from a removal port, that sample being clear of supply fluid and therefore representative of the patient's blood supply. The Gordon patent describes a method and apparatus for drawing blood from an injection site through an arterial line connected to a fluid supply.

The apparatus includes a variable capacity pump mechanism also having an interior chamber, first and second ports connected to the variable capacity interior chamber, and a retractable piston disposed within the housing to traverse within the chamber. A piston sealing member is provided about the chamber in slidable sealing relationship with the chamber to cause fluid to be drawn into the chamber, thereby facilitating extraction of the blood sample along the arterial line without the need to discharge an initial sample containing disproportionate amounts of supply fluid.

However, the Gordon device incorporates features which may be undesirable to a caregiver conducting the sampling process. For example, although the Gordon device is in fluid communication with the arterial lines transmitting fluid to the patient, the variable capacity chamber is disposed transverse to such line to cause an imbalance in such arterial line both prior to and during the sampling process. Moreover, the above-noted imbalance in the dual variable capacity storage device of Gordon is exacerbated during the sampling process making it difficult for a single attendant to conduct the sampling process. Although Gordon introduces certain desirable features to the sampling process, its awkward structure, and its bulkiness may be undesirable to the sampling process.

SUMMARY OF THE INVENTION

Accordingly, it would be desirable to provide a sampling device which introduces a certain symmetry to the sampling system to enable the sampling system to be readily used by a single attendant. Such a device would be readily integrated into the sampling system to be concentric with the arterial line extending from the patient to the fluid source. Moreover, such device should incorporate a sheath overlying the major elements of the sampling system to protect the system from outside contamination.

Further, the improved sampling device should incorporate a locking mechanism to limit the capacity of the sampling device. Further, the device should incorporate a swirl or vortex element to facilitate removal of blood and fluid from the sampling device when the blood and fluid in the device is returned to the patient and the device is flushed prior to reintroducing the fluid source to the patient.

Accordingly, the improved fluid storage mechanism comprises a cylindrical main body portion having a longitudinal axis generally aligned with the longitudinal axis of a fluid line of a blood sampling system. Disposed within the main body portion is a concentric fluid draw element in sealing relationship therewith and retractable along the longitudinal axis thereof. The fluid draw element includes a fluid conduit extending therethrough with a distal end of the conduit disposed adjacent to a first fluid port provided in the main body portion of the fluid storage mechanism with a second fluid port disposed at a proximal end of the fluid conduit in the fluid draw element.

The fluid storage mechanism also includes a vortex inducer element disposed at the distal end of the fluid conduit provided in the fluid draw element. The fluid draw element is retractable from a first position in which the main body portion receives the fluid draw element in a closed position of minimal fluid capacity to enable fluid flow from a fluid supply through the fluid conduit to the patient, to a continuously variable open position to enable withdrawal of fluid and blood into the storage mechanism to insure withdrawal of blood only at the sampling site.

Additional features of the improved fluid storage mechanism of the present invention includes a contamination sheath overlying the fluid storage mechanism to minimize external contamination of the mechanism during the sampling procedure. In the preferred embodiment of the invention the sheath is disposed between the fluid draw element and the main body portion of the fluid storage mechanism.

The improved fluid storage mechanism as described above is adapted to be disposed along the longitudinal axis of the arterial line extending from the fluid source to the injection site entering the patient. Moreover, such improved fluid storage mechanism includes a main body portion which is generally concentric with the arterial line, with the fluid draw element being concentric as well, thereby minimizing the ability of the device to tip or skew the line and further, enabling the single operator to more efficiently draw fluid and blood into the improved fluid storage mechanism and then to take a sample at the sampling site.

In another embodiment of the present invention, the fluid storage mechanism incorporates a pre-set volume feature which enables the sampling attendant to adjust the mechanism to a pre-set volume by a spiral groove or track on the fluid draw element cooperatively engaging a track guide provided on the interior of the main body portion. The track guide also serves as a locking mechanism which engages an outer edge of the sealing ring associated with the fluid draw element to limit the travel of the fluid draw element and the capacity of the fluid storage mechanism to a fixed maximum volume. Presetting the volume would allow the patient's blood pressure to fill the storage mechanism and minimize damage to the endothelium lining of the vein or artery receiving the catheter.

These and other advantages of the improved fluid storage mechanism will be better understood when the device is considered in light of the detailed description that follows, particularly when such description is considered in conjunction with the drawings provided.

DETAILED DESCRIPTION OF PREFERRED EMBODIMENT

Figure 1A:
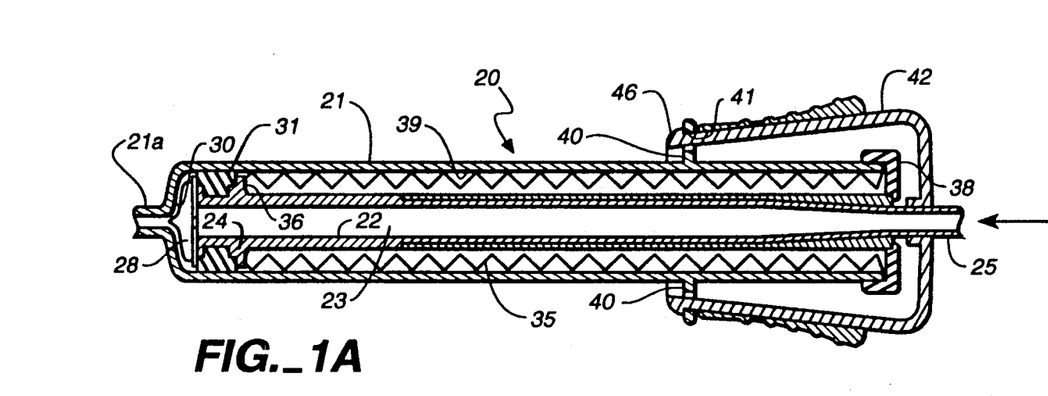
FIG. 1A is a sectional view of the improved fluid storage mechanism of the present invention in the fully closed position.
Figure 1B:
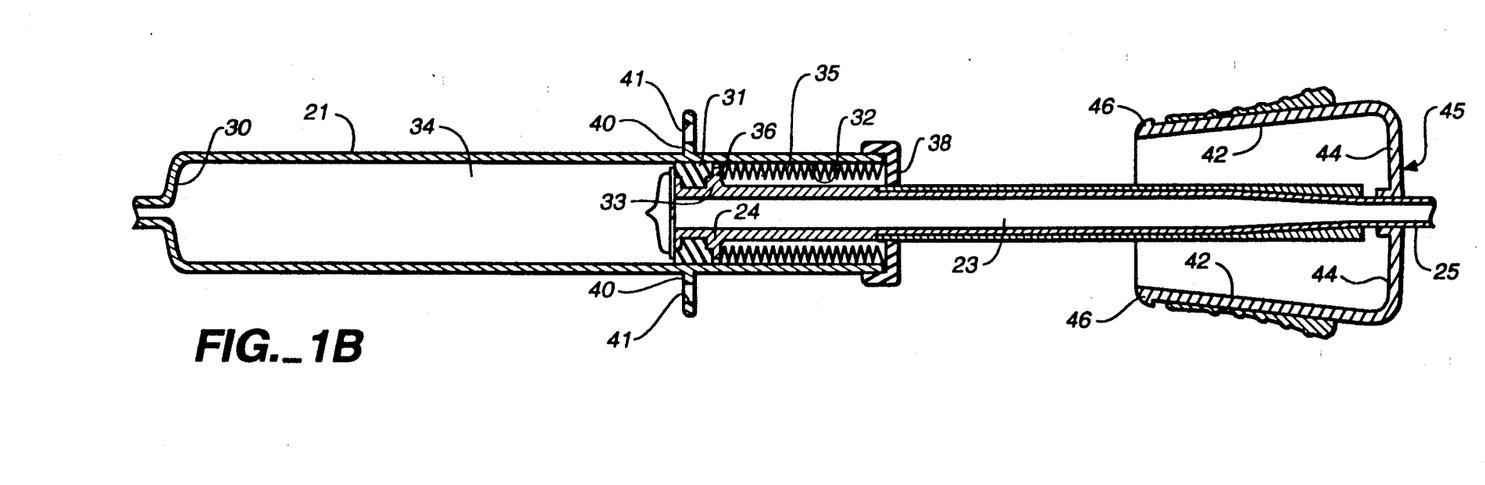
FIG. 1B is a view similar to FIG. 1A in which the fluid storage mechanism of the present invention has been fully extended to fill a storage chamber therein.

FIGS. 1A and 1B illustrate the preferred embodiment of the present invention. The present invention comprises an improved fluid storage mechanism 20 including a cylindrical main body portion 21, which tapers to a fluid receiving opening 21a at a distal end thereof and receives a cylindrical fluid draw element 22 concentrically mounted therein. Fluid conduit 23 extends through the fluid draw element 22 to terminate at a distal end 24 thereof and to continue at a proximal end 25 thereof through the fluid storage mechanism 20 to be connected to an external element 26 (FIG. 4A) associated therewith as better described below. Disposed at the distal end 24 of the fluid draw element 12 is a vortex inducer element 28 mounted thereon to overlie the distal end of fluid conduit 23.

In the fully closed position of the fluid draw element 12 the vortex inducer element 28 on the fluid draw element 22 is disposed adjacent the fluid receiving opening 21a at a tapered distal end 30 of the main body portion 21. The vortex inducer element 28 is described in greater detail below.

Adjacent the distal end of the fluid draw element 22 next to the vortex inducer element 28 is a sealing ring 31 which encircles the fluid draw element 22 and engages interior peripheral side wall 32 of the main body portion 21 to define a variable capacity fluid draw chamber 34 between the interior wall 32 of main body portion 21 and the sealing ring 31 of fluid draw element 22 of the fluid storage mechanism 20. Fluid draw chamber 34 is better seen in FIG. 1B.

A flexible anti-contamination sheath 35 is mounted on an exterior wall 33 of the fluid draw element 22 and the interior wall 32 of the main body portion 21 and is attached at the distal end to the fluid draw element at peripheral connection ring 36 and to the proximal end of the interior wall of the main body portion at peripheral connection ring 38.

The sheath 35 is comprised of a flexible material, such as a polyethylene which encircles the fluid draw element 22. In the preferred embodiment the sheath 35 shown in FIGS. 1A and 1B is pleated much like an accordion to expand in the fully open or extended position of the fluid flow mechanism 20 and to close in the fully closed position of the fluid flow mechanism 20. However, any thin flexible material could be employed and pleating of the sheath 35 is not necessary.

As seen in FIG. 1A, the fluid draw element 22 is locked in the fully closed position of the fluid flow mechanism 20 by the cooperation of retainers 40, which are rigidly mounted on opposite sides of the exterior of the main body portion 21 of the fluid flow mechanism 20, with clips 42. The retainers 40 include openings 41 extending therethrough. The openings 41 receive clips 42 which extend outwardly from the base 44 of a U-shaped bracket 45 which is mounted on the proximal end 25 of the fluid draw element 22. The clips 42 are biased outwardly and each terminate in a latching element 46 which is received in a respective opening 41 of a retainer 40 to secure the fluid draw element 22 in the fully closed position shown in FIG. 1A.

Figure 2:
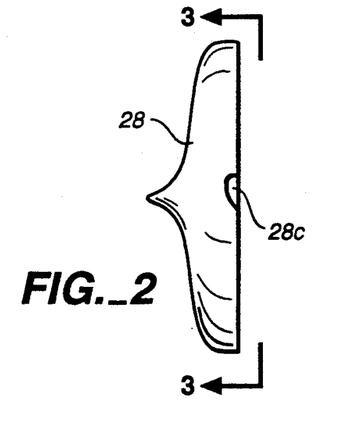
FIG. 2 is an enlarged side elevational view of a vortex inducer element of the improved fluid storage mechanism of the present invention.
Figure 3:
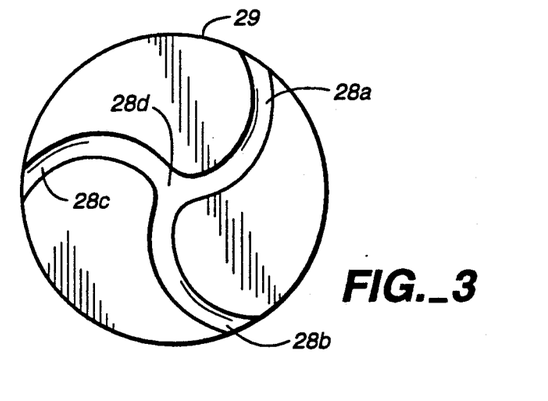
FIG. 3 is a view taken along the lines 3—3 of FIG. 2.

The vortex inducer element 28 is shown in greater detail in FIGS. 2 and 3 wherein grooves 28, 28b and 28c radiate from a central portion 28d of the element 28 to extend to a respective radial periphery 29 to provide a flow path from fluid conduit 23 into the fluid storage chamber 34. The outer surface of vortex inducer element 28 is tipped to conform generally to the interior of the tapered distal end 30 of the fluid chamber 34 of the fluid flow mechanism 20.

Figures 4A, 4B:
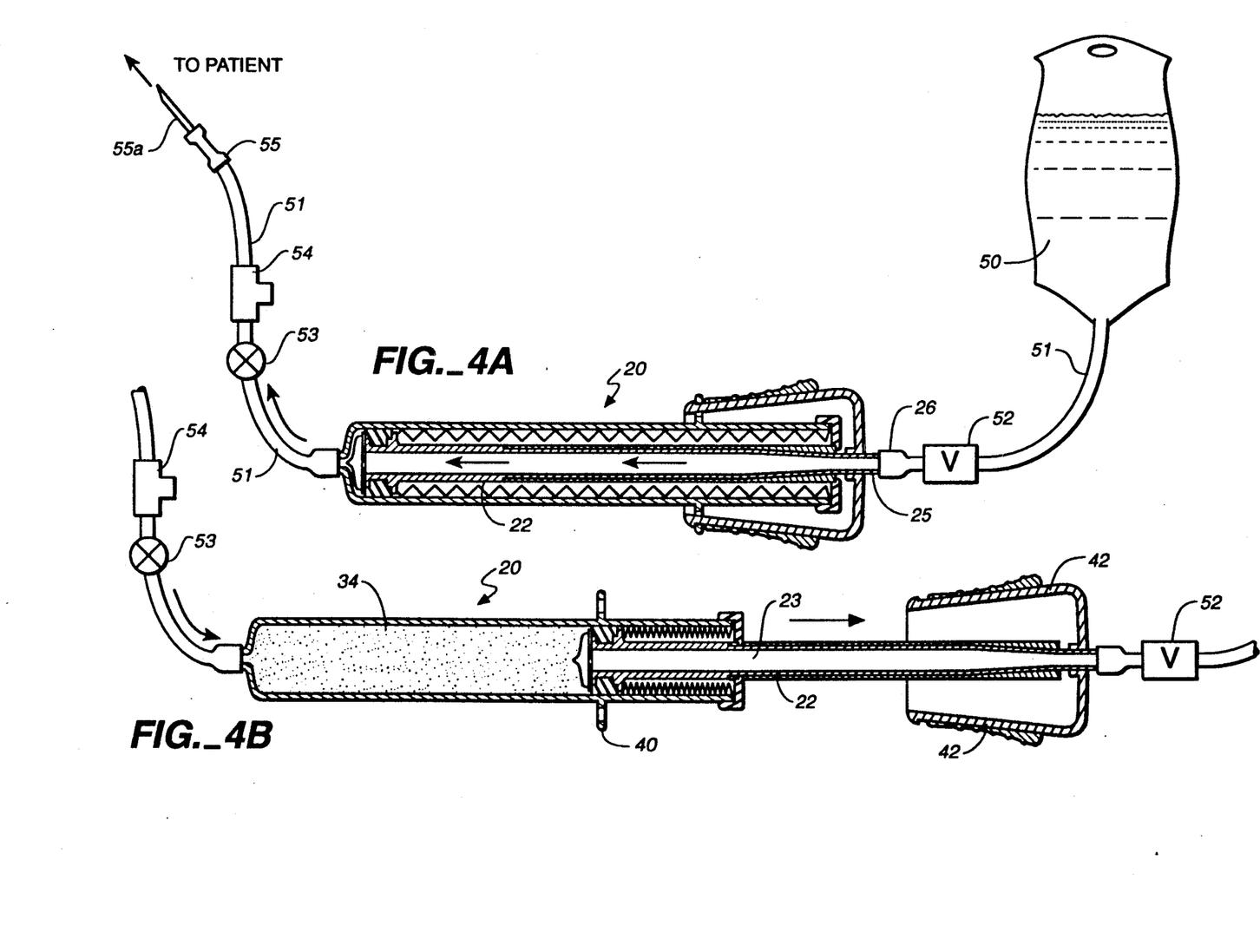
FIG. 4A is a representative sampling system incorporating the improved fluid storage mechanism of the present invention, with the fluid storage mechanism in a fully closed position.
FIG. 4B shows the sampling system with the fluid storage mechanism in a fluid draw or fully extended position.

A sampling system incorporating the fluid storage mechanism of the preferred embodiment of the present invention as shown in FIGS. 1-3 as shown in FIGS. 4A through 4F. In FIG. 4A, a fluid supply 50 is connected by an arterial line 51 to a variable flow control device and flush valve 52. Through an appropriate fitting 26 the flush valve 52 is connected to the proximal end 25 of the fluid storage mechanism 20. The fluid line 51 connected to the distal end of the fluid storage mechanism 20 is in turn connected to a shut-off valve 53 and then to a sampling port 54. Fluid line 51 also connects the sampling port 54 to an injection site 55 through which a catheter 55a is extended into the patient. In the closed position of FIG. 4A, fluid flow from the fluid supply 50, through the arterial line 51, through the flush valve 52, through the fluid storage mechanism 20 is at least at a keep-vein-open (K.V.O.) rate to maintain a positive flow of fluid from the fluid supply to the patient.

In FIG. 4B the fluid storage mechanism 20 is activated by releasing grips 42 from the brackets 40 to enable a fluid draw from the injection site in which fluid is drawn into the fluid storage chamber 34 of the fluid storage mechanism 20 with valve 53 open. When the storage chamber 34 of the mechanism 20 is filled, valve 53 is closed.

Figure 4C:
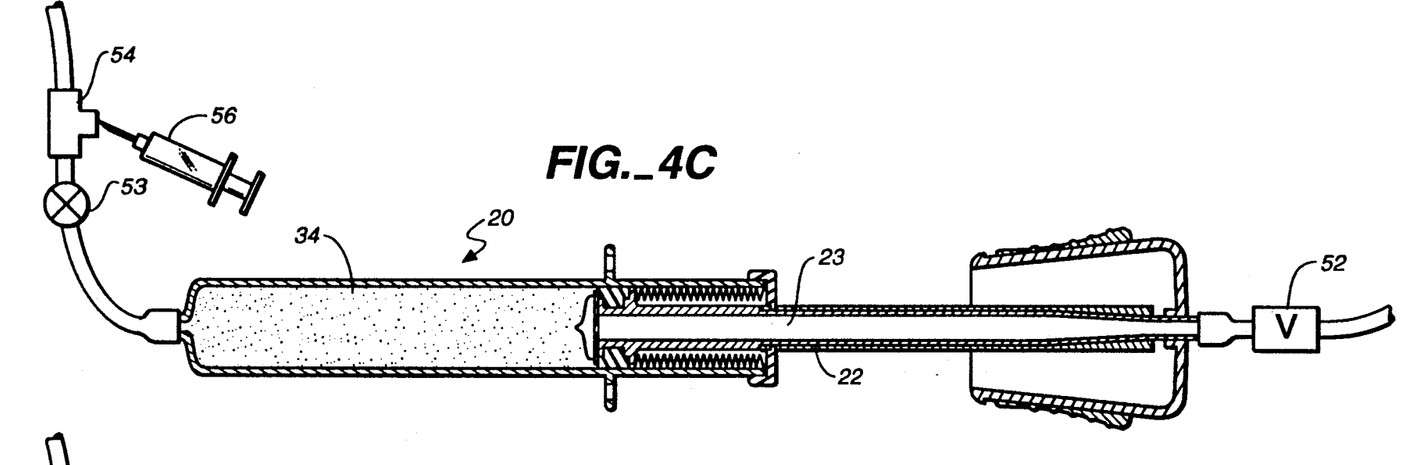
FIG. 4C shows a blood sampling procedure in progress with the fluid storage mechanism fully extended.

As shown in FIG. 4C, with valve 53 closed, a sampling container 56 is placed at the sampling port 54 to withdraw a blood sample from the patient through arterial line 51.

Figure 4D:
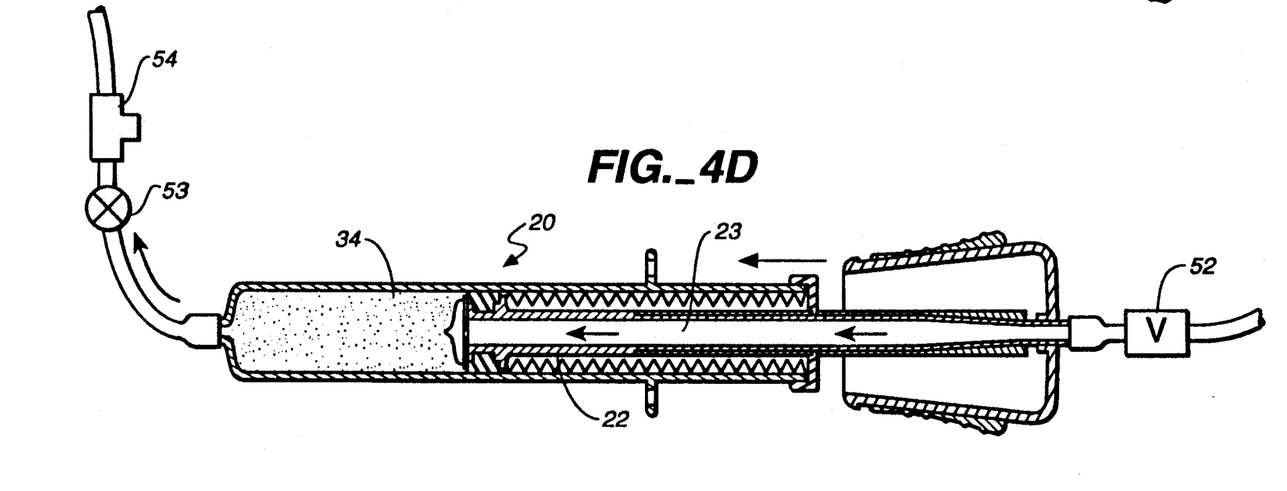
FIG. 4D shows the fluid storage mechanism at a mid-point of its return to the fully closed position.

As shown in FIG. 4D, once the sampling procedure is completed, the valve 53 is opened and the fluid draw element 22 is returned toward the fully closed position of the fluid storage mechanism 20, to transfer the fluid in the fluid draw chamber 34 back into the patient.

During the steps of the blood sampling procedure shown in FIGS. 4A-4D, flow continues to flow through the fluid conduit 23 of the blood draw element 22 at a low volume or "drip" flow rate. However, the vacuum effect produced by the extending of the fluid draw element 22, as in FIG. 4B, enables the arterial flow of blood and fluid from the patient to overcome the drip rate flow from fluid supply 50 and enter the fluid chamber 34 of the fluid flow mechanism 20.

Figure 4E:
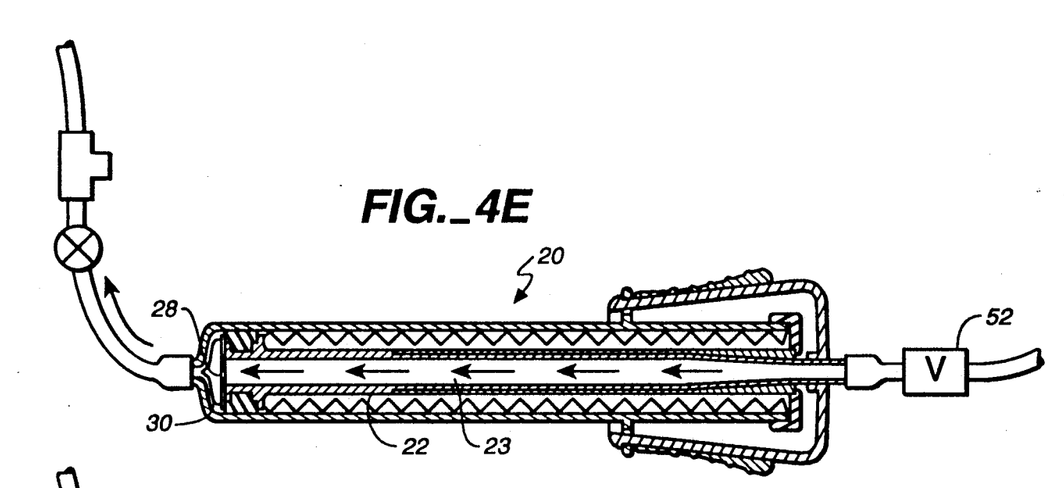
FIG. 4E shows the fluid storage mechanism in the fully closed position with a flush sequence in progress.

In FIG. 4E, with the fluid draw element 22 fully closed, variable rate valve 52 is activated at a high volume or flush rate to rapidly discharge any residual blood/fluid mixture from the distal end 30 of fluid chamber 34 of the fluid storage mechanism 20. The fluid flow through the fluid path of the vortex inducer element 28 creates a swirl effect at the distal end 30 of storage chamber 34 at the flush rate of the valve 52 to further assist removal of residual fluid from the fluid storage mechanism 20.

Figure 4F:
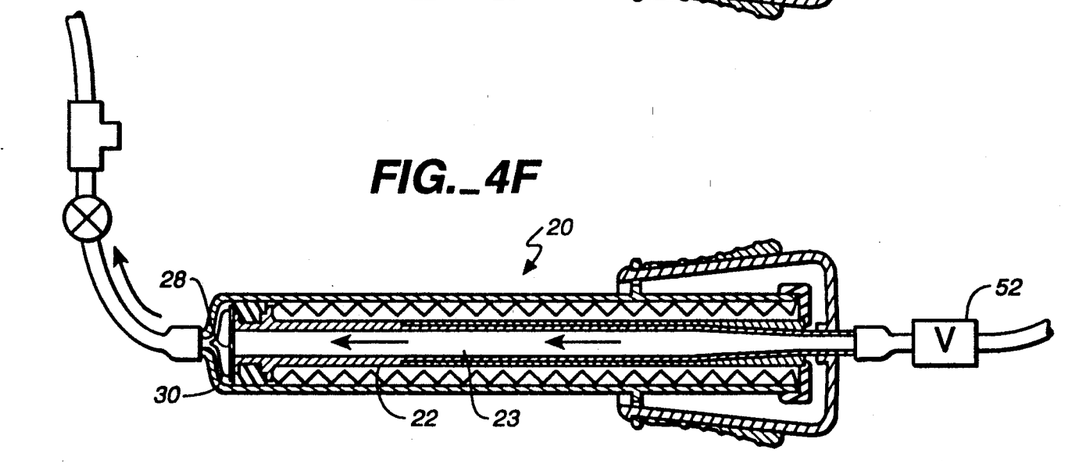
FIG. 4F shows the return of the fluid storage mechanism of the sampling system to the fully closed, low-volume flow position of FIG. 4A.

As shown in FIG. 4F, thereafter a low volume or drip infusion rate is resumed by the valve 52, to continue infusion of fluids into the patient.

Figure 5:
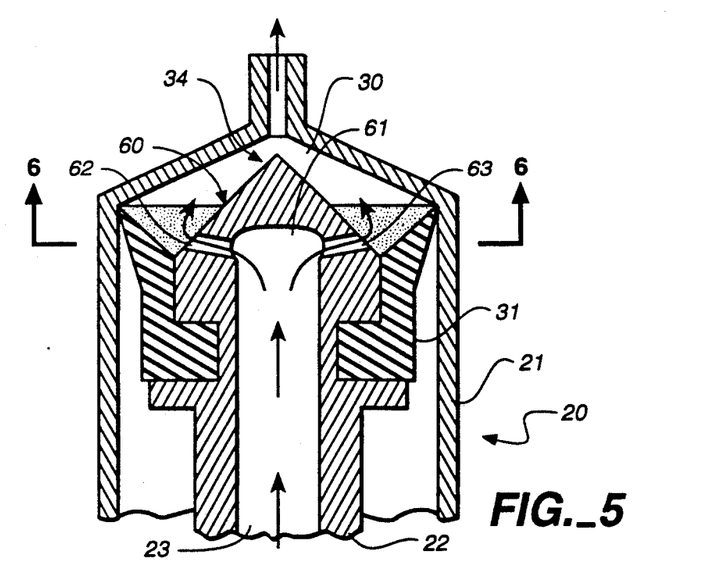
FIG. 5 is a broken line section of the distal end of the fluid storage mechanism wherein is incorporated a first alternative embodiment of the vortex inducer element of FIG. 2.
Figure 6:
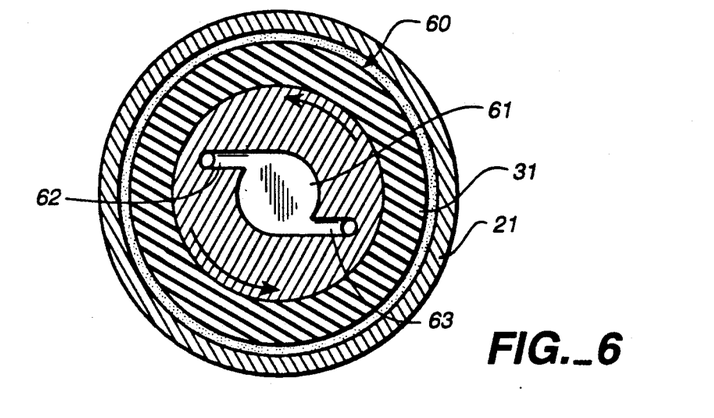
FIG. 6 is a view taken along lines 6—6 of FIG. 5.

The embodiment of the vortex inducer element 28 shown in FIGS. 2 and 3 is not the only embodiment available to the user. For example, as shown in FIGS. 5 and 6, the main body portion 21 of the fluid flow mechanism 20 could incorporate at its distal end 30 a fluid draw element 22 having a fluid conduit 23 therethrough and including a vortex inducer element 60, having a central opening 61 extending from the fluid conduit 23, and having provided on opposite sides of that central opening 61 oppositely facing channels 62 and 63, so as to induce a swirl effect of vortex type flow in the distal end 30 of the fluid chamber 34 of the fluid flow mechanism 20. Circumferential sealing member 31 closes one end of the chamber 34.

Figure 7:
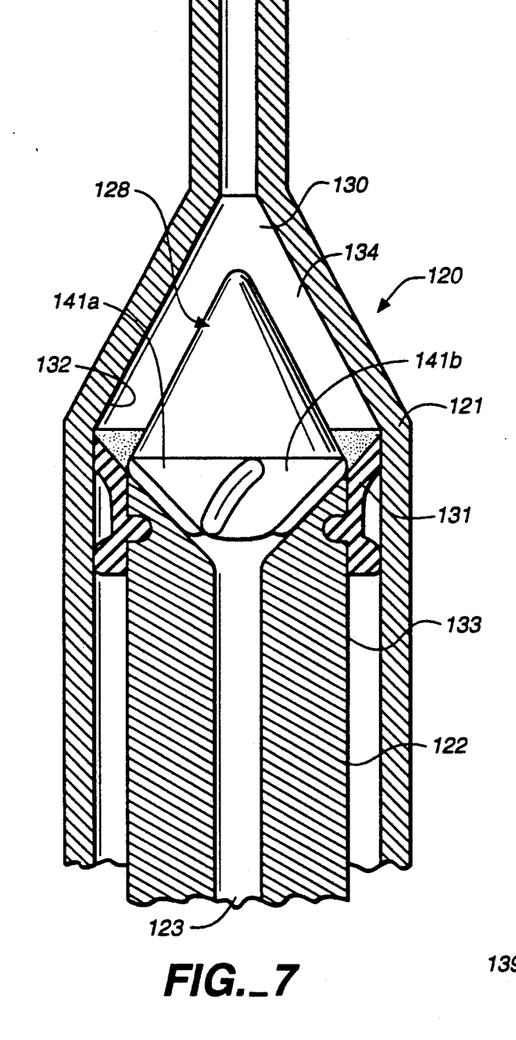
FIG. 7 is a broken line section of the distal end of the storage mechanism wherein is incorporated a second alternative embodiment of the vortex inducer element of FIG. 2.
Figure 8:
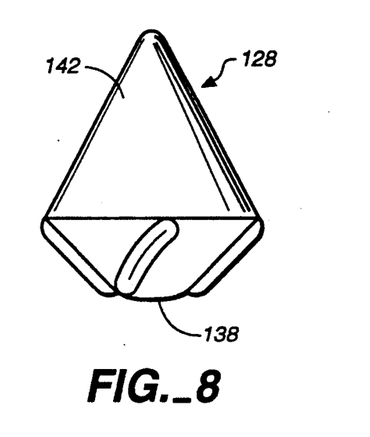
FIG. 8 is a side elevational view of the vortex inducer element of FIG. 7.
Figure 9:
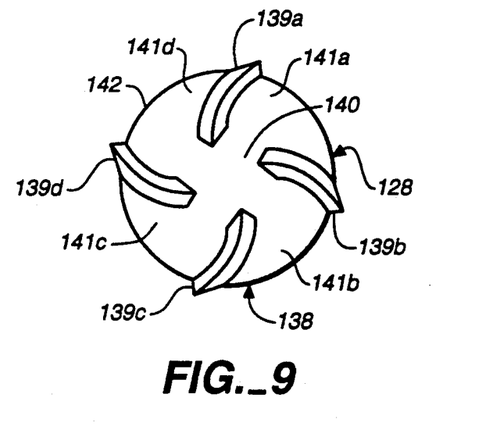
FIG. 9 is a bottom view of the vortex inducer element shown in FIG. 8.

In FIGS. 7-9 a second alternative embodiment of the vortex inducer element of the present invention is shown within a fluid flow mechanism 120 having a main body portion 121, and the fluid storage chamber 134 is defined between a sealing member 131 and interior wall 132 of the main body portion. Disposed within the main body portion 121 is a fluid draw element 122 having a fluid conduit 123 therein with the sealing ring 131 disposed between the outer wall 133 of the fluid draw element 122 and the inner wall 132 of the main body portion 121 with a vortex inducer element 128 mounted at the distal end of the fluid draw element 122 to define multiple fluid paths 141a and 141b at the distal end of the fluid draw element 122.

Vortex inducer element 128 is better seen in FIGS. 8 and 9. An upper face 142 conforms generally to the distal end 130 of the fluid storage mechanism 120. At the bottom or base 138 of the vortex inducer element 128 are a plurality of ribs 139a, 139b, 139c and 139d. The ribs 139a,b,c,d radiate from a central bottom portion 140 to a peripheral edge 142 to define between the ribs 139 and the base 138 of the vortex inducer element 128 fluid flow channels 141a, 141b, 141c and 141d. Although a preferred embodiment and two alternative embodiments of the vortex inducer element have been shown, it is to be understood that other embodiments are possible and that the alternative embodiments may not be restricted to grooves alone or ridges alone, but may be a combination of the two.

Figure 10:
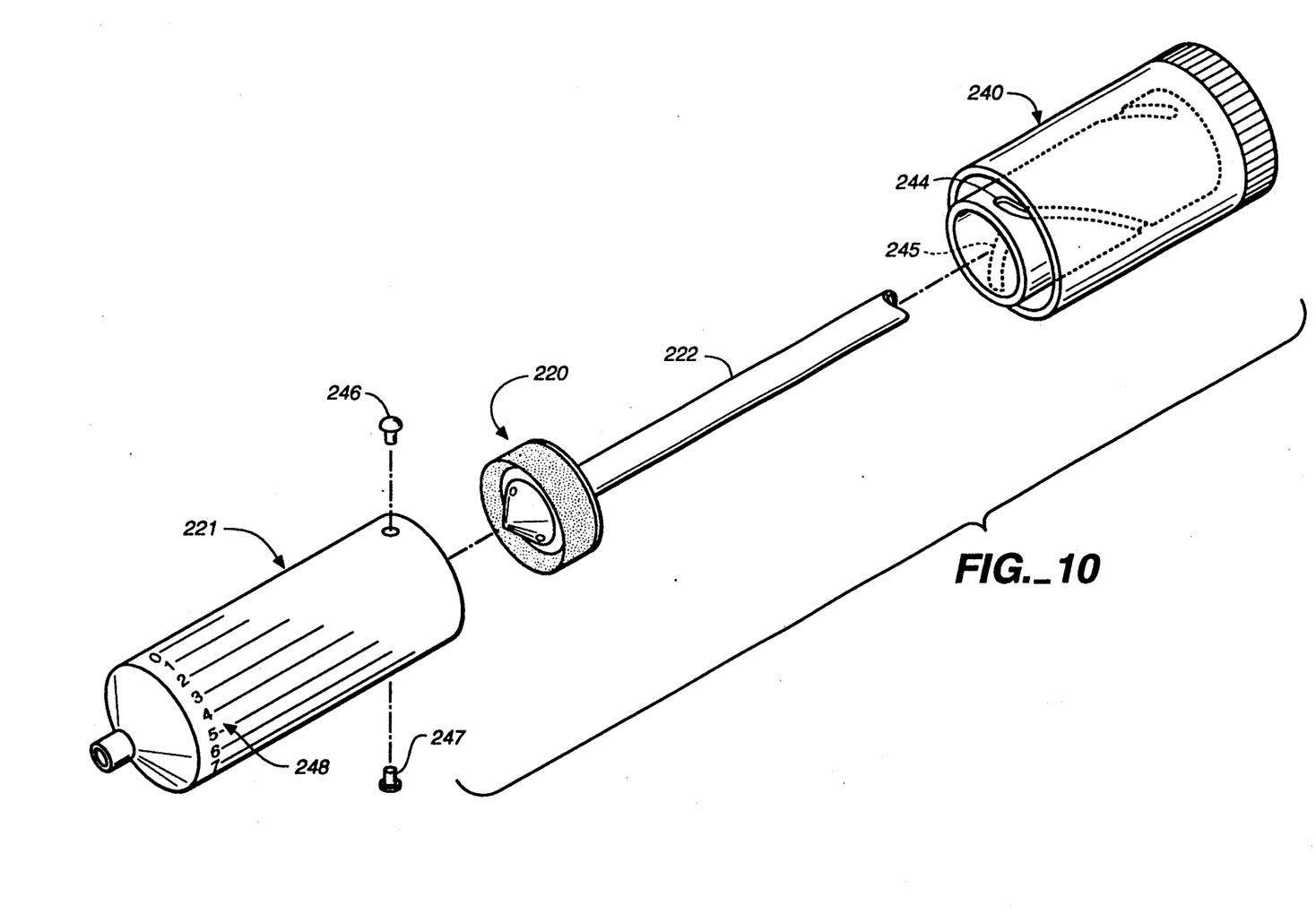
FIG. 10 is an exploded perspective view of an alternative embodiment of the fluid storage mechanism of FIG. 1, the alternative embodiment incorporating a volume control feature.
Figure 11A:
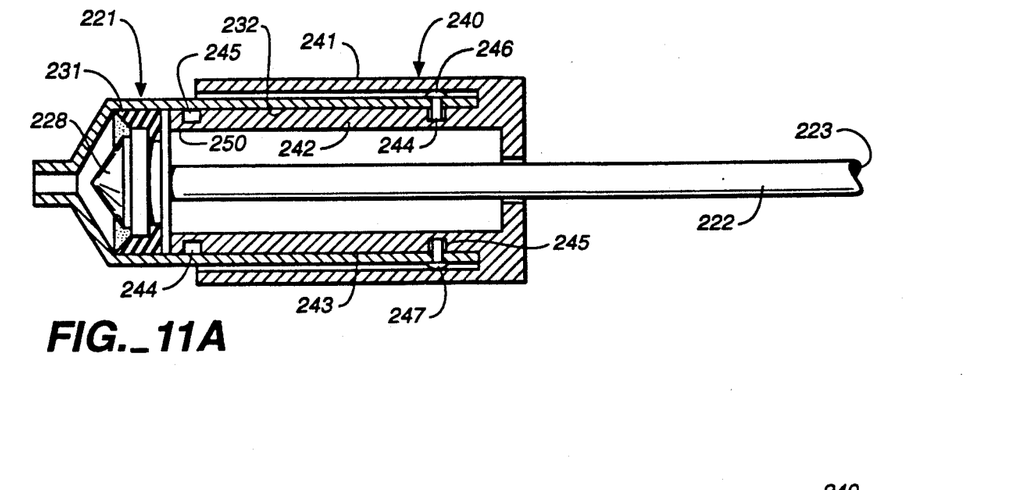
FIG. 11a is a side elevational in section of the alternative embodiment of FIG. 10, with the fluid draw element and the volume control element fully closed.
Figure 11B:
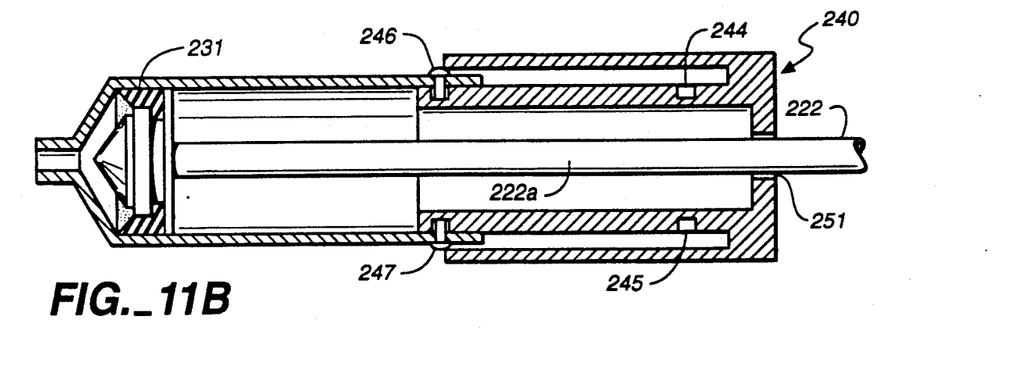
FIG. 11b is a sectional side elevation similar to FIG. 11a in which the volume control element is fully extended and the fluid draw element is fully closed.
Figure 11C:
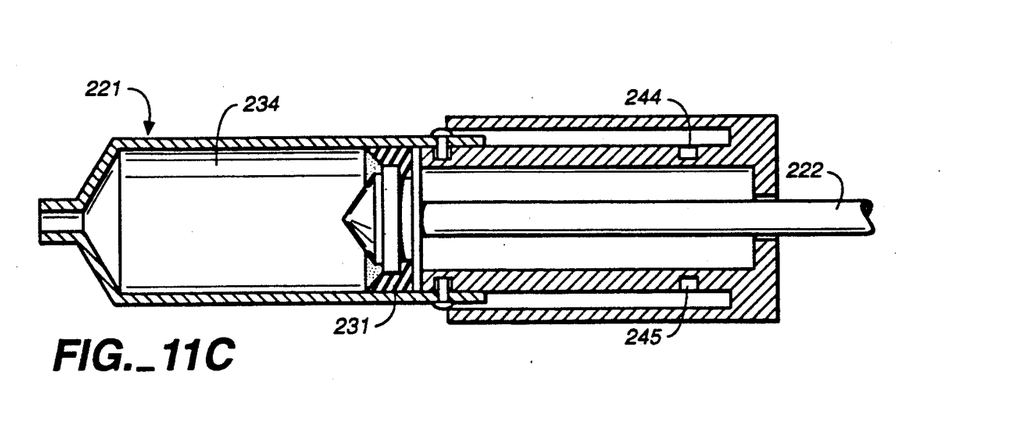
FIG. 11c is a sectional side elevation of the fluid storage mechanism of the alternative embodiment in which the volume control element and the fluid draw element are both fully extended.

As shown in FIGS. 10 and 11, the fluid storage mechanism of the present invention may also incorporate a volume control feature. For example, a fluid flow mechanism 220 includes a main body portion 221, a fluid draw element 222 having a fluid conduit 223 therein, a vortex inducer element 228 at the distal end of the fluid draw element 222 and a circumferential sealing ring 231 disposed at the distal end of the fluid draw element 222, with a fluid storage chamber 234 defined between the main body portion 221 and the sealing ring 231 of fluid draw element 222.

In the alternative embodiment of FIGS. 10 and 11, disposed behind the sealing ring 231 of the fluid draw element 222 is a volume control device 240 having an outer cylindrical deanti-contamination shell 241 and a cylindrical volume control shell 242 disposed within the circumferential interior wall 232 of the main body portion 231. Provided on the exterior wall 243 of the cylindrical shell 242 are a pair of spiral grooves 244 and 245 displaced 180° apart as beet seen in FIG. 10. Received in the grooves 244 and 245 are respective groove or track guides 246 and 247.

Provided on the exterior of the main body portion 221 and associated with the fluid chamber 234 is a set of markings 248 to indicate the volume gradations as the volume control device 240 is moved along grooves 244, 245 from the fully closed position of the fluid storage mechanism 220 to the fully extended position of the fluid storage mechanism 220. The fluid draw element 222 has a longitudinal body portion 222a slideably received in a rear opening 251 in the volume control device 240.

The operation of the fluid storage mechanism 220 is better seen in FIGS. 11a through 11c. In FIG. 11a, the fluid storage mechanism 220 is shown in the fully closed position, with the fluid draw element fully closed and the volume control device 240 engaged against a bottom wall 250 of the fluid draw element 222.

In FIG. 11b, the volume control device 240 is withdrawn away from end wall 250 of the fluid draw element 222 to the extreme end of tracks 244 and 245 with the fluid draw element 222 remaining at the fully closed position.

With the volume control device 240 withdrawn away from the bottom of the fluid draw element 222, there is no force to retain the fluid draw element in place and the arterial flow from the patient forces the fluid draw element backward until the bottom wall 250 of the fluid draw element engages the end of the fluid control device 240 as seen in FIG. 11c. Although the volume control device 240 was set at an extreme end position for illustrative purposes in FIGS. 11a through 11c, such volume control device could be set at any intermediate position to preset a specific volume for the fluid chamber 234.

The above description sets forth the preferred embodiment of the present invention and those alternatives known to the inventor. It is to be understood that various modifications and additions may be made to the preferred embodiment without departing from the spirit and scope of the present invention. Such modifications as may be obvious to one skilled in the art may be implemented to adapt the present invention for use in conjunction with a variety of different applications. However, the scope of the present invention is to be defined by the claims set forth below.

We claim:

1. A blood sampling system including a fluid line extending from a fluid supply to a patient, said system comprising an injection site entering the patient at a distal end of the fluid line, a fluid container disposed at the proximal end of the fluid line, a sampling site disposed proximally of the injection site, means enabling fluid flow from the fluid supply at variable rates, and a fluid storage mechanism interposed between the sampling site and the fluid supply to facilitate sampling, the fluid storage mechanism comprising:

a main body portion having a longitudinal axis thereof generally aligned with the longitudinal axis of the fluid line;

a concentric fluid draw element disposed within said main body portion in sealing relationship therewith and retractable along the longitudinal axis thereof;

a fluid path provided through the fluid storage mechanism including a first fluid port provided in the main body portion;

a fluid conduit provided in the fluid draw element extending from a distal end disposed adjacent said first fluid port to a proximal end thereof; and a vortex inducer element mounted at the distal end of the fluid conduit provided in the fluid draw element and having a fluid path therethrough, said vortex inducer element comprising a disk-like member having an upper surface and lower surface, the upper surface generally terminating at a point to conform its shape to the shape of the distal end of the main body portion of the fluid storage mechanism, and a lower surface including at least one groove radially extending from the center of the disk to an outer periphery of the disk, the groove spiralled from is central inner end to its radial outer end to induce a spiral flow of fluid from the distal end of the fluid conduit in the fluid draw element and into the fluid storage chamber of the fluid storage mechanism, with the fluid draw element retractable from a first sealed position, in which the main body portion receives the fluid draw element in a closed position of minimal fluid capacity to enable fluid flow from the fluid supply through the fluid conduit to the patient, to a continuously variable open position to enable withdrawal of blood and fluid into the fluid storage mechanism to assure withdrawal of blood only at the sampling site, and returnable to the closed position to return the fluids therein to the patient, with activation of the fluid flow means at a flush rate for cleansing blood and fluid from the fluid storage mechanism of the blood sampling system.

2. A blood sampling system as claimed in claim 1 wherein the fluid flow enabling means is disposed adjacent the fluid supply between the fluid storage mechanism and the fluid supply.

3. A blood sampling system as claimed in claim 1 wherein the fluid draw element of the fluid storage mechanism includes a sealing member disposed adjacent the distal end thereof and a longitudinal segment retaining the fluid conduit therein and extending generally along a longitudinal axis of the main body portion of the fluid storage mechanism.

4. A blood sampling system as claimed in claim 1 wherein the lower surface of the vortex inducer element includes a plurality of spiral grooves emanating from a central portion of the lower surface and extending outwardly to a peripheral edge thereof.

5. A blood sampling system as claimed in claim 1 wherein said at least one groove comprises three spiral grooves equally spaced at the peripheral edge of the lower surface of the vortex inducer element.

6. A blood sampling system as claimed in claim 1 wherein the main body portion of the fluid storage mechanism includes volume gradations marked thereon, a volume control device having at least one spiral groove provided therein and extending from a distal end to a proximal end of the volume control device, and a rack guide protruding inwardly of the main body portion and engaging the spiral groove in the volume control device, the volume control device receiving the fluid draw element in cooperative relation, whereby the engagement of the track guide in the groove of the volume control device at a fixed position enables controlled extension of the fluid draw element from the main body portion of the fluid storage mechanism, thereby to enable entry of a pre-set volume of fluid from the patient into the fluid storage mechanism.

7. A blood sampling system including a fluid line extending from a fluid supply to a patient, said system comprising an injection site entering the patient at a distal end of the fluid line, a fluid container disposed at the proximal end of the fluid line, a sampling site disposed proximally of the injection site, means enabling fluid flow from the fluid supply at variable rates, and a fluid storage mechanism interposed between the sampling site and the fluid supply to facilitate sampling, the fluid storage mechanism comprising:

a main body portion having a longitudinal axis thereof generally aligned with the longitudinal axis of the fluid line;

a concentric fluid draw element disposed within said main body portion in sealing relationship therewith and retractable along the longitudinal axis thereof;

a fluid path provided through the fluid storage mechanism including a first fluid port provided in the main body portion;

a fluid conduit provided in the fluid draw element extending from a distal end disposed adjacent said first fluid port to a proximal end thereof; and a vortex inducer element mounted at the distal end of the fluid conduit provided in the fluid draw element and having a fluid path therethrough, said vortex inducer element including upper and lower faces and disposed on the lower face thereof is a central portion having fluid channels disposed at opposite ends thereof with a first fluid channel extending to one peripheral edge of the element and a lower fluid channel extending to an opposite peripheral edge of the lower face, to dispose exit ports of the fluid channels approximately 180° apart, with the fluid draw element retractable from a first sealed position, in which the main body portion receives the fluid draw element in a closed position of minimal fluid capacity to enable fluid flow from the fluid supply through the fluid conduit to the patient, to a continuously variable open position to enable withdrawal of blood and fluid into the fluid storage mechanism to assure withdrawal of blood only at the sampling site, and returnable to the closed position to return the fluids therein to the patient, with activation of the fluid flow means at a flush rate for cleansing blood and fluid from the fluid storage mechanism of the blood sampling system.

8. A blood sampling system including a fluid line extending from a fluid supply to a patient, said system comprising an injection site entering the patient at a distal end of the fluid line, a fluid container disposed at the proximal end of the fluid line, a sampling site disposed proximally of the injection site, means enabling fluid flow from the fluid supply at variable rates, and a fluid storage mechanism interposed between the sampling site and the fluid supply to facilitate sampling, the fluid storage mechanism comprising:

a main body portion having a longitudinal axis thereof generally aligned with the longitudinal axis of the fluid line;

a concentric fluid draw element disposed within said main body portion in sealing relationship therewith and retractable along the longitudinal axis thereof;

a fluid path provided through the fluid storage mechanism including a first fluid port provided in the main body portion;

a fluid conduit provided in the fluid draw element extending from a distal end disposed adjacent said first fluid port to a proximal end thereof; and a vortex inducer element mounted at the distal end of the fluid conduit provided in the fluid draw element and having a fluid path therethrough, said vortex inducer element comprising upper and lower faces, with the upper face generally conforming to the distal end of the main body portion of the fluid storage mechanism and the lower face including a plurality of ridges therein, each of said ridges extending from an open central portion of the bottom face and extending to a peripheral edge thereof with a plurality of fluid channels, each defined between each successive pair of ridges provided on the vortex inducer element, with the fluid draw element retractable from a first sealed position, in which the main body portion receives the fluid draw element in a closed position of minimal fluid capacity to enable fluid flow from the fluid supply through the fluid conduit to the patient, to a continuously variable open position to enable withdrawal of blood and fluid into the fluid storage mechanism to assure withdrawal of blood only at the sampling site, and returnable to the closed position to return the fluids therein to the patient, with activation of the fluid flow means at a flush rate for cleansing blood and fluid from the fluid storage mechanism of the blood sampling system.

9. A blood sampling system including a fluid line extending from a fluid supply to a patient, said system comprising an injection site entering the patient at a distal end of the fluid line, a fluid container disposed at the proximal end of the fluid line, a sampling site disposed proximally of the injection site, means enabling fluid flow from the fluid supply at variable rates, and a fluid storage mechanism interposed between the sampling site and the fluid supply to facilitate sampling, the fluid storage mechanism comprising:

a main body portion having a longitudinal axis thereof generally aligned with the longitudinal axis of the fluid line;

a concentric fluid draw element disposed within said main body portion in sealing relationship therewith and retractable along the longitudinal axis thereof;

an anti-contamination sheath attached to an exterior distal end of the fluid draw element and a proximal end of the main body portion of the fluid storage mechanism to prevent contamination of the fluid sample drawn into the fluid storage mechanism from an external source;

a fluid path provided through the fluid storage mechanism including a first fluid port provided in the main body portion;

a fluid conduit provided in the fluid draw element extending from a distal end disposed adjacent said first fluid port to a proximal end thereof; and a vortex inducer element mounted at the distal end of the fluid conduit provided in the fluid draw element and having a fluid path therethrough, with the fluid draw element retractable from a first sealed position, in which the main body portion receives the fluid draw element in a closed position of minimal fluid capacity to enable fluid flow from the fluid supply through the fluid conduit to the patient, to a continuously variable open position to enable withdrawal of blood and fluid into the fluid storage mechanism to assure withdrawal of blood only at the sampling site, and returnable to the closed position to return the fluids therein to the patient, with activation of the fluid flow means at a flush rate for cleansing blood and fluid from the fluid storage mechanism of the blood sampling system.

* * * * *